United States Patent [19]

Schmidt et al.

[11] Patent Number: 5,418,220
[45] Date of Patent: May 23, 1995

[54] METHOD FOR TREATING CONSTIPATION USING DIMETHICONE

[76] Inventors: Alfred Schmidt, Leinpfad 2, 22301 Hamburg; Hans-Jürgen Upmeyer, Mauerkircherstr. 197, 81925 München, both of Germany

[21] Appl. No.: 207,070

[22] Filed: Mar. 8, 1994

[51] Int. Cl.$^6$ ............... A61K 31/695; A61K 31/74
[52] U.S. Cl. ........................ 514/63; 424/78.08; 514/892
[58] Field of Search ............. 514/892.63; 424/78.08

[56] References Cited

U.S. PATENT DOCUMENTS 3,275,509  9/1966  Rowan et al. .................. 167/56

FOREIGN PATENT DOCUMENTS

| | | |
|---|---|---|
| 68566 | 1/1983 | European Pat. Off. . |
| M5549 | 4/1966 | France . |
| 2017735 | 5/1970 | France . |
| 2017736 | 5/1970 | France . |
| 3807712 | 2/1989 | Germany . |
| 80/00658 | 4/1980 | WIPO . |

OTHER PUBLICATIONS

Hein et al. Ger DE 3807712 (Feb. 2, 1989) CA. 111:453289.
Byk-Gulden (I)/FR. 2017736 (May 22, 1970) GA 74:79620M.
Byk-Gulden (II) FR. 2017735 (May 22, 1970) GA 74:146401f.
Grimberg WO/PCT 8000658 (Apr. 17, 1980) Derwent.
Roberti FR 5549M (Apr. 14, 1966) Derwent.
Rowon U.S. 3275504 (Apr. 24, 1963) Derwent.

*Primary Examiner*—Shep Rose
*Attorney, Agent, or Firm*—Wenderoth, Lind & Ponack

[57] ABSTRACT

The invention disclosed relates to the use of dimethicone as an agent for treating constipation.

8 Claims, No Drawings

METHOD FOR TREATING CONSTIPATION USING DIMETHICONE

TECHNICAL FIELD OF THE INVENTION

The invention relates to methods for treating constipation.

BACKGROUND OF THE INVENTION

Constipation means a delay in the discharge of dry and hard feces. It is caused either by a delayed passage of the stomach contents through the intestine or a disorder of the evacuation reflex. Possible reasons for the delayed passage through the intestine are dietetic factors, changes in the intestinal walls or a functional or organic disorder of the nervous system. Also, pharmaceuticals may have a constipating effect. A defect in the defecation mechanism is found in disorders of the anal channel, in the case of loss of the rectal dilation reflex or a weakness in the abdominal muscles used to apply abdominal pressure. Patients complain about symptoms such as a sensation of pressure, flatulence, and pains during the discharge of feces.

Constipation is treated with laxatives which on the one hand soften the hard feces and on the other hand prompt defecation.

Laxatives either act as lubricants, fillers or swelling agents, have saline or osmotic properties, or produce an anti-absorptive or secretagogue effect. The substances of the afore-mentioned groups are combined in commercial preparations in many ways.

When used in long-term therapy, almost all laxatives, except for the swelling agents, increasingly cause disorders of the electrolyte metabolism and in particular cause a potassium loss, which in turn increases constipation. The sodium loss can be so high as to cause a secondary hyperaldesteronism. The potassium losses so caused may lead to a reduced intestine motility and may increase constipation. Moreover, hypokalaemias are above all dangerous when used in therapy together with cardiac glycosides. Concomitant calcium losses can promote the occurrence of osteoporosis, especially in women.

The administration of a swelling agent involves the danger that the stomach contents might stick together, from which the danger of an ileus ensues.

Moreover, many laxatives are resorbed, with the result that they can have a large number of systemic side effects.

Hence, there has been a need for an effective agent for treating constipation which does not produce the aforementioned side effects and consequently lends itself for use in problem patients, for instance children, immobile or geriatric patients and women, in particular during pregnancy.

SUMMARY OF THE INVENTION

According to the invention, dimethylpolysiloxane (dimethicone) was found to be effective in the treatment of constipation, without producing the usual side effects.

Commercial dimeticone-containing preparations are used to treat indications such as flatulence, sensation of repletion (bloating) and meteorism. Moreover, the use of dimeticone for treating inflammatory and ulcerous diseases of the esophagus, the stomach and the duodenum has been described.

DETAILED DESCRIPTION OF THE INVENTION

Dimethylpolysiloxane may be administered to a human or animal in the form of tablets, capsules, emulsions, suspensions and powders for oral administration or in combination with foodstuffs and dietary supplements. Such compositions may be administered to humans and animals in a safe and effective amount to elicit the desired result. The compositions used for this invention typically comprise an effective amount of dimethylpolysiloxane and a biologically acceptable carrier. Such carriers may be solid or liquid, such as, for example, highly dispersed silicon dioxide, cornstarch, lactose, saccharose, glucose, sucrose, water, water and fat emulsions such as glycerin stearate emulsions and flavoring agents. If a solid carrier is used, the dosage forms may be tablets, capsules or lozenges. Liquid dosage forms include soft gelatine capsules, syrup or liquid suspension. The dimeticone-containing compositions may be employed according to this invention in a conventional manner for the treatment and prevention of constipation. Their dosage levels may be chosen by those of ordinary skill in the art from the available methods and techniques. Specific dosage and treatment regimens will depend upon factors such as health status and the severity and course of constipation and disposition thereto.

In order that this invention be more fully understood, the following example is set forth. This example is for the purpose of illustration only, and is not to be construed as limiting the scope of the invention in any way.

EXAMPLE

Preparation of treatment composition 2 kg of dimethylpolysiloxane containing approximately 60 g of highly dispersed silicon dioxide was heated in a water bath to about 70° C. 1 kg of solid, finely triturated glycerin stearate (a mixture of mono- and diglycerin stearate) was then added thereto and the mixture was left in the water bath until the entire mass had melted. The mixture was then stirred to form an emulsion to which 3 liters of water were slowly added at a temperature of about 70° C. After further stirring and gradual cooling, a stable aqueous emulsion formed which had a stiff, lard-like composition at room temperature. This composition could now be finely dosed, admixed with an inert tabletting mass consisting of saccharose, glucose, lactose and flavoring agents, and made into tablets. It is also possible to dilute the resulting mass with water to prepare a liquid preparation for administration as drops.

Application of treatment composition sex: female
age: 2 years
diagnosis: constipation
additional symptoms: tibia fracture (left side) resulting in a bed-ridden condition
duration of constipation: three days
concomitant symptoms: non-specific symptomatic pains
therapy: one teaspoon of the dimethicone suspension
result: complete evacuation of the fetes (bowels) after two hours As the patient was required to remain immobilized, the situation after three further days was the same as before treatment. Again, about 40 drops (one teaspoon)

of the dimeticone suspension was administered. After the suspension was allowed to act for 2 hours, it produced a complete evacuation of the bowels.

While we have described an embodiment of this invention, it is apparent that our embodiment may be altered to provide other embodiments which utilize the method of this invention. Therefore, it will be appreciated that the scope of this invention is to be defined by the appended claims, rather than by the specific embodiment which has been presented by way of example.

We claim:

1. A method for treating constipation consisting essentially of administering a constipation reducing amount of dimethylpolysiloxane in combination with a biologically acceptable carrier to a human or animal having constipation.

2. The method according to claim 1 wherein the dimethylpolysiloxane is administered in combination with a highly dispersed silicon dioxide.

3. The method according to claim 1 wherein the dimethylpolysiloxane is administered in combination with a biologically acceptable emulsifier.

4. The method according to claim 3, wherein the dimethylpolysiloxane is administered in combination with a highly dispersed silicon dioxide.

5. The method according to claim 3, wherein the emulsifier is glycerine stearate.

6. The method according to claim 4, wherein the emulsifier is glycerine stearate.

7. The method according to claim 1, wherein the animal is a human being.

8. The method according to claim 7, wherein the human being is a child, immobile or geriatric patient, or a pregnant woman.

* * * * *